United States Patent [19]

Hagen et al.

[11] Patent Number: 5,114,424
[45] Date of Patent: May 19, 1992

[54] MULTIPART PLANAR ELECTRODE FOR AN HF-SURGERY DEVICE

[75] Inventors: Uwe Hagen, Forchheim; Peter Feucht, Berlin, both of Fed. Rep. of Germany

[73] Assignee: Siemens Aktiengesellschaft, Berlin and Munich, Fed. Rep. of Germany

[21] Appl. No.: 572,259

[22] Filed: Aug. 27, 1990

[30] Foreign Application Priority Data

Sep. 7, 1989 [EP] European Pat. Off. ........ 89116574.8

[51] Int. Cl.⁵ ............................................. A61B 17/39
[52] U.S. Cl. ....................................... 606/32; 128/798
[58] Field of Search .................... 606/32, 35; 128/639, 128/644, 734, 798

[56] References Cited

U.S. PATENT DOCUMENTS

| | | | |
|---|---|---|---|
| 3,380,445 | 4/1968 | Frasier . | |
| 3,534,727 | 10/1970 | Roman . | |
| 3,720,209 | 3/1973 | Bolduc | 128/639 |
| 3,750,649 | 8/1973 | Severinghaus | 128/734 |
| 3,888,240 | 6/1975 | Reinhold, Jr. et al. | 128/644 |
| 4,381,789 | 5/1983 | Naser et al. . | |
| 4,448,199 | 5/1984 | Schmid | 128/639 |
| 4,619,266 | 10/1986 | Hodgson | 128/798 |

FOREIGN PATENT DOCUMENTS

| | | | |
|---|---|---|---|
| 1219642 | 3/1987 | Canada . | |
| 0262888 | 4/1988 | European Pat. Off. . | |
| 0308690 | 3/1989 | European Pat. Off. . | |
| 394385 | 4/1924 | Fed. Rep. of Germany . | |
| 3509975 | 10/1986 | Fed. Rep. of Germany . | |
| 3544443 | 6/1987 | Fed. Rep. of Germany . | |
| 3623293 | 1/1988 | Fed. Rep. of Germany . | |
| 3718585 | 12/1988 | Fed. Rep. of Germany . | |
| 1441622 | 7/1976 | United Kingdom . | |
| 1587817 | 4/1981 | United Kingdom | 128/639 |

*Primary Examiner*—Lee S. Cohen
*Attorney, Agent, or Firm*—Hill, Van Santen, Steadman & Simpson

[57] ABSTRACT

A multipart planar electrode, suitable for use as a neutral electrode for an HF surgery device, has four sub-electrodes arranged on one side of a flexible, common carrier. At least three of these sub-electrodes have substantially the same area and at least two of the sub-electrodes have a limiting edge disposed parallel to and adjacent at least a portion of a separate edge of one of the remaining sub-electrodes. This insures that, if one of the sub-electrodes is used as an auxiliary electrode for a symmetry measurement of sub-currents, there will not be equality of the contact area of the electrodes with the patient's skin at the remaining sub-electrodes upon the occurrence of a straight-line release edge in an arbitrary direction. Because such equal areas will not occur, this will be detected by the symmetry measurement and an alarm indicating partial detachment of the electrode can be activated.

10 Claims, 1 Drawing Sheet

MULTIPART PLANAR ELECTRODE FOR AN HF-SURGERY DEVICE

BACKGROUND OF THE INVENTION

1. Field of the Invention

The present invention is directed to a planar electrode having a plurality of sub-electrodes, of the type suitable for use as a neutral electrode for an HF surgery device, the sub-electrodes being disposed on one side of a flexible, common carrier.

2. Description of the Prior Art

Planar electrodes having a plurality of sub-electrodes of substantially the same size arranged on one side of a flexible-common carrier are described, for example, in European Application 0 308 690, German OS 36 23 293, and German OS 37 18 585. Monitoring circuits are standard in HF-surgery devices to avoid burning the patient upon the occurrence of an unintentional, partial removal (detachment) of the electrode from the body of the patient. If the electronic outlay for the monitoring circuit, which may for example measure sub-currents of each electrode, is to maintained low, one of the sub-electrodes of the multi-part electrode must be used as an auxiliary electrode for supplying an auxiliary current. Such measurements are based on the knowledge that sub-electrodes of identical size form sub-currents which are also of substantially the same size, given current flow with full-surface application of the electrodes on the skin of the patient. This is known as a symmetry measurement.

Experience has shown that an undesired detachment of the electrode from the body of the patient usually occurs along a release edge which proceeds on a straight line. On a case-by-case basis, such a release edge may intersect two of the sub-electrodes of the type known in the prior art and be oriented such that the remaining surfaces of both of the sub-electrodes which are still in contact with the patient's skin have equal areas. Since the currents from these partial areas will also be substantially the same size, a conventional symmetry measurement will not recognize that such a partial detachment has occurred.

SUMMARY OF THE INVENTION

It is an object of the present invention to provide a multipart electrode having a plurality of sub-electrodes configured and oriented so that a conventional symmetry measurement can be undertaken which will recognize even partial detachment of the multipart electrode from the patient along a straight release line oriented in any direction.

The above object is achieved in a multipart planar electrode constructed in accordance with the principles of the present invention wherein at least four sub-electrodes are disposed on one side of a common, flexible carrier, one of the sub-electrodes forming an auxiliary electrode for conducting a symmetry measurement, and the remaining sub-electrodes being of substantially the same area. At least two neighboring sub-electrodes are disposed with respective identical limiting edges disposed parallel and adjacent to at one portion of a separate circumferential line of the remaining sub-electrode. Given the sub-electrode configuration of the invention, and the selection of any one of the sub-electrodes as the auxiliary electrode, an equality of contact area at the remaining sub-electrodes, given a release edge proceeding on a straight line in an arbitrary direction, cannot occur, because of the spatial relationship of the four sub-electrodes to each other.

DESCRIPTION OF THE PREFERRED EMBODIMENTS

Figure 1:
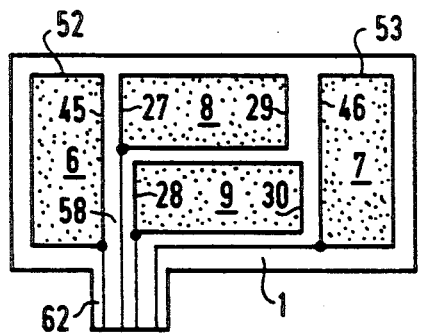
FIGS. 1 through 5 respectively show plan views of a multipart electrode constructed in accordance with the principles of the present invention in five different embodiments.

A first embodiment of a multipart planar electrode constructed in accordance with the principles of the present invention is shown in FIG. 1. In this embodiment, four rectangular sub-electrodes 6, 7, 8 and 9 are disposed on one side of a rectangular, flexible carrier 1. The two neighboring sub-electrodes 8 and 9 have limiting edges 27 and 28 arranged parallel and adjacent to a section 45 of a circumferential edge 52 of the sub-electrode 6. The sub-electrodes 8 and 9 have further identical limiting edges 29 and 30 arranged parallel to and adjacent a section 46 of a circumferential edge 53 of the other sub-electrode 7. The sub-electrodes 8 and 9 are electrically isolated and are arranged in the central region of the carrier 1. In this embodiment, all of the sub-electrodes 6 through 9 are rectangular and have the same area, so that any one of the sub-electrode can be used as the auxiliary electrode for conducting a symmetry measurement. Regardless of which sub-electrode is used as the auxiliary electrode, it is insured that, given a straight-line release edge occurring in an arbitrary direction, no portion of the surface of any sub-electrode remaining in contact with the patient will be equal in size to the remaining contacting area of any of the other sub-electrodes. Since there will no longer by symmetrical conditions, a conventional symmetry monitoring system will be able to recognize such a partial detachment even taking tolerances due, for example, to different skin resistances into consideration. For example, the sub-electrodes 6 through 9 may be connected to an HF surgery device via a connecting line, these connecting lines meeting on a projection 62 which forms a terminal for connection to the surgery device. The projection 62 is preferably arranged in the region of separation 58 between the outer electrodes 6 and 7.

Figure 2:
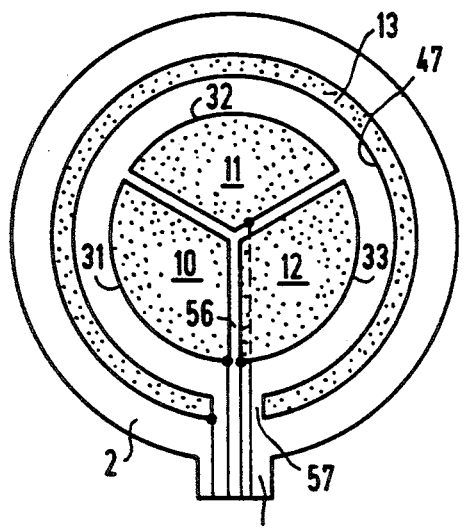

A further embodiment of the invention is shown in FIG. 2 wherein the electrodes are arranged on a round carrier 2. Three sub-electrodes 10, 11 and 12 having the same area are arranged in a central region of carrier 2 as electrically isolated segments of a circular surface. This geometrical surface is concentrically surrounded by an annular sub-electrode 13. The identical outer limiting edges 31, 32 and 33 of the respective sub-electrodes 10, 11 and 12, which are arcuately curved in this embodiment, are arranged on a circumferential edge (not separately identified) of the circular area covered by the sub-electrodes 10, 11 and 12. The edges 31, 32 and 33 are parallel to and adjacent the inner circumferential edge 47 of the annular sub-electrode 13. The sub-electrode 13 is used as the auxiliary electrode, and need not be of the same area as the sub-electrodes 10, 11 and 12. As a result, symmetrical current flow from the sub-electrode 13 through the body tissue of the patient to the sub-electrodes 10, 11 and 12 results. The annular sub-electrode 13 has a gap 57, adjacent to which a separation location 56 between the two sub-electrodes 10 and 12 is disposed. As a result, electrical connection via the projection 63 to all sub-electrodes can be achieved in a simple manner.

Figure 3:
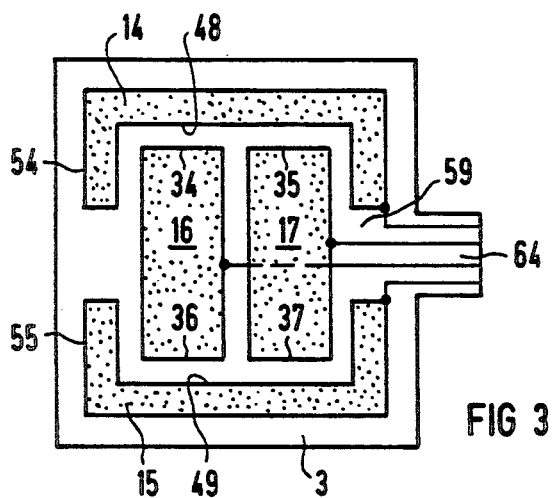

A further embodiment of the electrode of the invention is shown in FIG. 3. In this embodiment, two rectangular sub-electrodes 16 and 17 are disposed adjacent each other on a square area in the center of a square carrier 3. Two further sub-electrodes 14 and 15 are disposed outside of the central region, and are adjacent and electrically isolated from the sub-electrodes 16 and 17. A section 48 of a circumferential edge 54 of the sub-electrode 14 is parallel and adjacent limiting edges 34 and 35 of neighboring sub-electrodes 16 and 17. The same is true for the section 49 of the circumferential edge 55 of the sub-electrode 15 with respect to limiting edges 36 and 37 of the sub-electrodes 16 and 17. A projection 64 for an electrical terminal is again provided in the region of the separation location 59 for the outer electrode.

Figure 4:
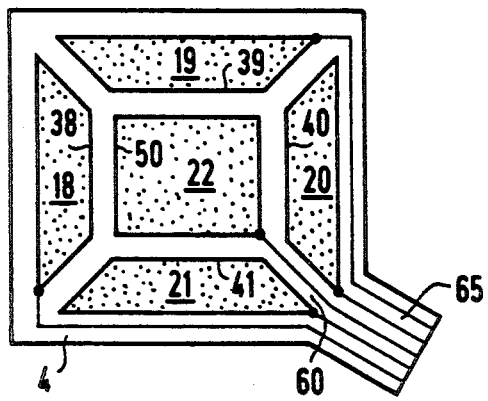

Another embodiment is shown in FIG. 4, wherein five sub-electrodes are arranged in a rectangular, preferably square carrier 4. Electrodes 18, 19, 20 and 21 neighboring each other have respective identical limiting edges 38, 39, 40 and 41 which are arranged parallel and adjacent to respective sections of the circumferential edges 50 of a centrally disposed, rectangular (preferably square) inner sub-electrode 22. If the inner sub-electrode 22 is not of the same area as each of the outer sub-electrodes 18 through 21, the inner sub-electrode 22 will be used as the auxiliary electrode because of the symmetrical current distribution which can be achieved. Because the inner electrode 22 is surrounded by a ring consisting of four sections and matched to the shape of the inner electrode 22, a total of five electrical lines at the projection 65 are required, the projection 65 being disposed in the region of any one of the separation locations between the outer electrode, such as location 60 in the embodiment of FIG. 4.

Figure 5:
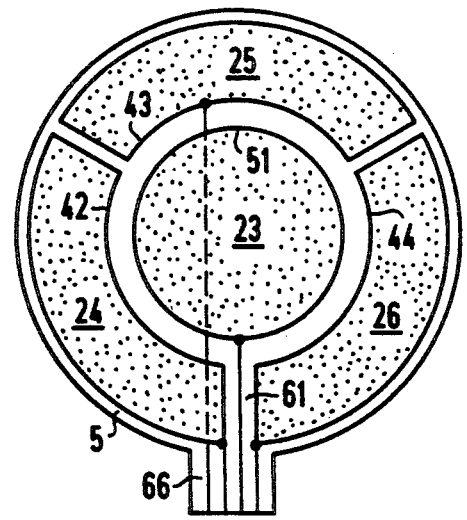

Another embodiment using only four sub-electrodes is shown in FIG. 5. In this embodiment, a circular sub-electrode 23 is used as the auxiliary electrode, and is disposed in a central region of a circular carrier 5. The sub-electrode 23 is surrounded by a concentric ring of three segments separated from each other and forming outer sub-electrodes 24, 25 and 26. The sub-electrodes 24, 25 and 26 have arcuately curved, identical limiting edges 42, 43 and 44, which are arranged parallel and adjacent to a circumferential edge 51 of the sub-electrode 23. Due to the rotationally symmetrical arrangement of the sub-electrodes 24 through 26 relative to the central auxiliary electrode 23, current relationships which are particularly symmetrical are achieved when the entire areas of each of the sub-electrodes are respectively in contact with the patient. The normally-occurring symmetry of the electrode arrangement of FIG. 5 is so good that the occurrence of a straight-line release edge proceeding in an arbitrary direction across the electrode of FIG. 5 is detectable at a very early point in time, so that very small detachments can be recognized early with a simple electronic circuit. In the embodiment of FIG. 5, a projection 66 forming the electrical terminal is arranged in the separation region 61 between outer electrodes 24 and 26.

The embodiment of FIG. 5 can be manufactured in a space-saving way, and can be arranged on the patient without special precautions so that a largely uniform distribution of the HF energy proceeding from the operating field onto the sub-electrodes is achieved. This latter condition is also valid for the embodiments of FIGS. 2, 3 and 4, because all of the sub-electrodes are arranged substantially symmetrically relative to an imaginary axis which, in the middle regions of the respective carriers 2 through 5, is disposed perpendicularly relative to the common plane of the sub-electrodes. The equal areas of the neighboring sub-electrodes 8 and 9, 10 through 12, 16 and 17, and 24 through 26 can be achieved in an especially simple manner if each of these sub-electrodes has an electrode separation location, for example location 56 in FIG. 2, formed by straight-line limiting edges, and if the separation location has a longitudinal extent disposed perpendicularly relative to the respective adjacent section of the circumferential edge of the allocated adjacent electrode. For example, the separation location 58 in the embodiment of FIG. 1 has a longitudinal extent which is perpendicular to the circumferential edge 45, and a similar relationship is present in each of the other embodiments.

As used herein, "identical limiting edges" means that two neighboring or adjacent edges of two respective electrode surfaces have coinciding or identical features. For example, in FIG. 1 the limiting edges 27 and 28 of the sub-electrodes 8 and 9 have the following identical features. Both edges 27 and 28 proceed in the same direction (vertically), both edges 27 and 28 are of the same length, both edges 27 and 28 are shorter than the horizontal reference edges (not provided with reference numerals), and both edges 27 and 28 form the left limitation of the sub-electrodes 8 and 9. In the embodiment of FIG. 2, the limiting edges 31 through 33 of the sub-electrodes 10 through 12 have the following identical features. The edges 31 through 33 proceed in the circumferential direction of a circular area, the edges 31 through 33 are of the same length, the edges 31 through 33 are longer than the remaining limiting edges (not provided with reference numerals) at the sub-electrodes 10 through 12, and the edges 31 through 33 form the outer limitation of the sub-electrodes 10 through 12.

Multipart electrodes constructed in accordance with the principles of the present invention can also be used in combination with more complex electronic monitoring circuits, for example circuits for undertaking impedance measurements, so that the electrodes are compatible with many different types of HF surgery devices having different types of monitoring circuits.

All of the sub-electrodes disclosed in the various embodiments, except for electrodes 14 and 15, consist of regular geometrical shapes or areas, such as rectangles, squares, trapezoids, circles or segments of a circle. As used herein the term "geometrical area" therefore means an area of conventional, regular geometric shape.

Although modifications and changes may be suggested by those skilled in the art, it is the intention of the inventors to embody within the patent warranted hereon all changes and modifications as reasonably and properly come within the scope of their contribution to the art.

We claim as our invention:

1. A multipart planar electrode for use as a neutral electrode in an HF surgery device comprising a flexible carrier; and at least four sub-electrodes disposed on a side of said carrier, at least one of said four sub-electrodes being disposed in a central region of said carrier, with the remainder of said at least four sub-electrodes being arranged outside of said central region of said carrier, said remainder of said at least four sub-electrodes being disposed adjacent and electrically isolated from said sub-electrode disposed in said central region of said carrier, at least three of said sub-electrodes having substantially the same area, and said at least three sub-electrodes including at least two neighboring sub-electrodes having respective, identical adjacent limiting edges disposed parallel to at least a portion of a limiting edge of one of the other of said four sub-electrodes.

2. An electrode as claimed in claim 1 wherein all of said sub-electrodes are disposed symmetrically relative to an imaginary axis extending perpendicularly through a middle of said carrier.

3. An electrode as claimed in claim 1 wherein said limiting edges of said at least two neighboring sub-electrodes are disposed on the circumference of a geometrical area.

4. An electrode as claimed in claim 3 wherein said circumference is arcuately curved.

5. An electrode as claimed in claim 1 wherein at least one of said four sub-electrodes has a shape different from the shape of the other sub-electrodes.

6. An electrode as claimed in claim 5 wherein said differently shaped sub-electrode has a circumferential edge corresponding to the circumference of a geometrical area.

7. An electrode as claimed in claim 1 wherein said four sub-electrodes include a circular sub-electrode arranged in a central region of said carrier, said circular sub-electrode being surrounded by a concentric ring consisting of three ring sections separated from each other, said three ring sections forming three neighboring sub-electrodes.

8. An electrode as claimed in claim 1 wherein said four sub-electrodes include a rectangular sub-electrode arranged in a central region of said carrier, said rectangular sub-electrode being surrounded by a square concentric ring of four segments, said four segments forming four neighboring sub-electrodes.

9. An electrode as claimed in claim 8 wherein said rectangular sub-electrode is a square sub-electrode.

10. An electrode as claimed in claim 1 further comprising a projection in said carrier from which electrical lines proceeding to each of said sub-electrodes proceed, said projection forming a terminal adapted for connection to a monitoring circuit.

* * * * *